United States Patent [19]

Borghi

[11] Patent Number: 5,336,251
[45] Date of Patent: Aug. 9, 1994

[54] ADAPTOR DEVICE FOR UNIPOLAR ELECTRODE CATHETERS

[75] Inventor: Enzo Borghi, Budrio, Italy

[73] Assignee: X-Trode S.r.l., Bologna, Italy

[21] Appl. No.: 3,440

[22] Filed: Jan. 12, 1993

[30] Foreign Application Priority Data

Jun. 9, 1992 [IT] Italy .................. B092A 000233

[51] Int. Cl.⁵ .................................................. A61N 1/05
[52] U.S. Cl. .................................... 607/116; 439/909; 604/280; 604/283
[58] Field of Search ................ 128/784, 786, 419 P, 128/642, 420.6; 604/280, 283, 264; 439/909

[56] References Cited

U.S. PATENT DOCUMENTS 4,583,543  4/1986  Peers-Trevarton ............ 128/419 P
4,954,106  9/1990  Fischer ........................... 128/786

Primary Examiner—William E. Kamm
Assistant Examiner—Brian M. Green
Attorney, Agent, or Firm—Fay, Sharpe, Beall, Fagan, Minnich & McKee

[57] ABSTRACT

A replacement cardiac pacemaker is connected to an already implanted electrode catheter from which the original connecting pin has been discarded, and the cut end of the severed spiral wound wire bared from its sheath, by an adaptor that comprises a sleeve accommodating a conductive spindle rotatable about its own axis and rigidly associated with a coaxial stilet projecting from an open socket end of the sleeve and insertable tightly into the bore of the bared wire; the sleeve also accommodates a second spiral wound wire interposed between the sleeve and the corresponding section of the stilet, attached by its ends respectively to the socket end and to the spindle, and a detachable key by means of which the spindle can be rotated in such a way as to subject the second wire to a torsional stress that results in the first wire being restrained against the stilet. The interlocked wires and stilet are encapsulated in an insulating outer sheath and made secure with surgical threads bound firmly around the sheath.

11 Claims, 4 Drawing Sheets

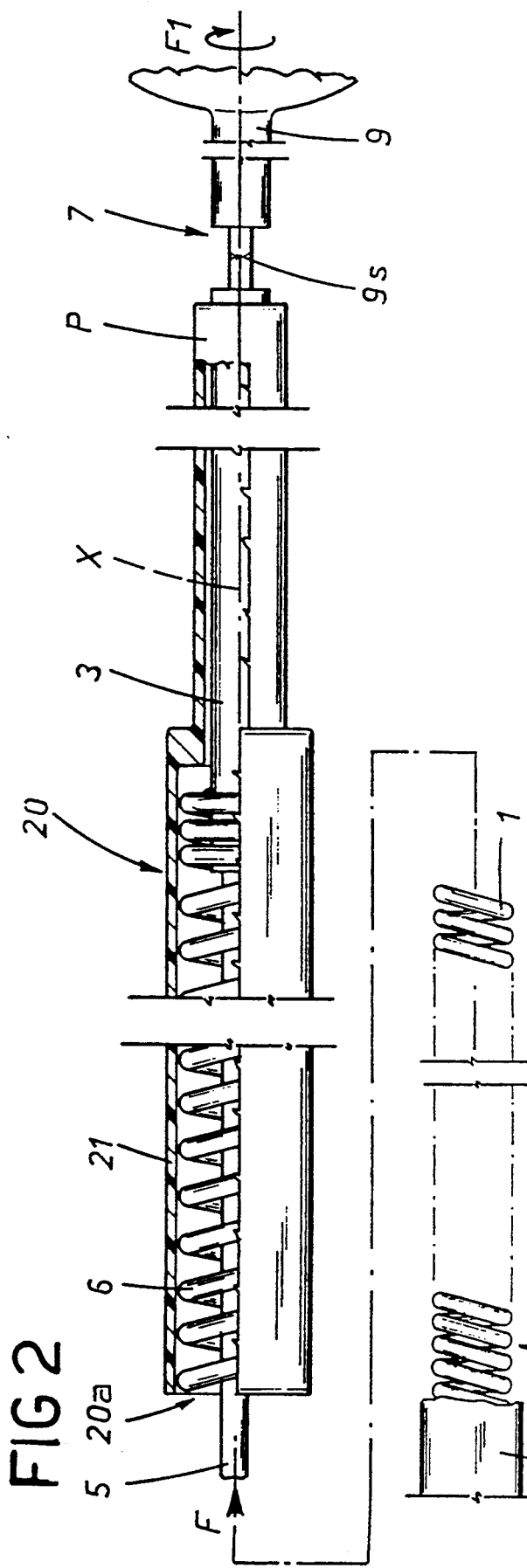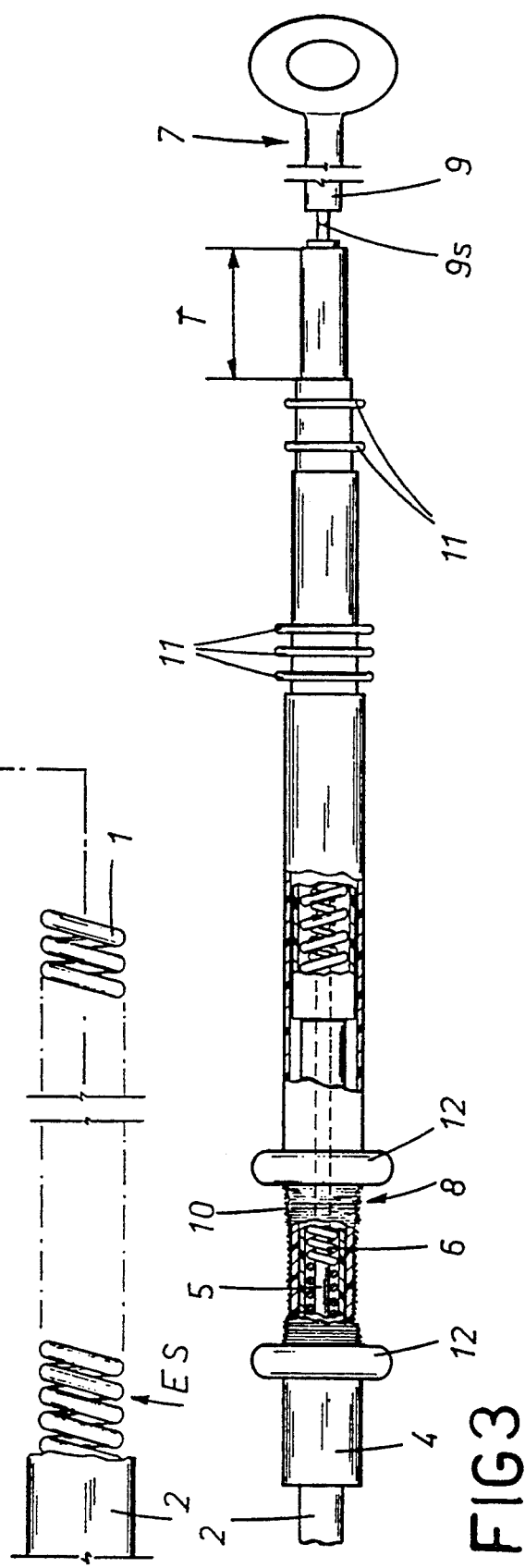

ADAPTOR DEVICE FOR UNIPOLAR ELECTRODE CATHETERS

BACKGROUND of the INVENTION

The present invention relates to an adaptor device for electrode catheters, in particular for unipolar electrode catheters.

The art field of heart surgery embraces numerous types of cardiac catheter designed for connection at one end, generally by way of a flexible tube functioning as a biocompatible outer sheath, to an artificial pacemaker implanted in the body of the patient, and carrying a terminal electrode at the remaining end which is offered in direct contact (positively anchored in most instances), to the ventricular cardiac muscle.

In the particular case in point, the expression 'unipolar' is used to describe a catheter of which the terminal electrode constitutes the negative pole or cathode of the cardiac pacemaker, and the positive pole or anode is provided by the casing of the pacemaker itself. The terminal or ventricular electrode consists in a sharp point, preferably affording elements such as will penetrate and thus establish a continuous and secure contact with the cardiac muscle, connected to the negative pole of the pacemaker by way of an electrically conductive spiral wound wire (e.g. platinum-iridium alloy). It is being found currently, where patients require the replacement of an existing pacemaker rendered unreliable by reason of its low charge, irregular operation or malfunction, that problems can arise due to incompatibilities between the connectors of electrode catheters implanted in the past and those of more recent design; reflecting the ever greater technological advances being made in this field, in effect, the newer catheters are much smaller than their predecessors as the overall dimensions of the newer pacemakers also become much smaller.

Remembering that the ventricular electrode becomes embedded in time beneath a layer of organic tissue and cannot be removed (such a step is inadvisable from the medical standpoint), it happens that the solution adopted in present-day surgical practice is almost invariably one of implanting a completely new electrode catheter in the cardiac cavity for connection to the new pacemaker, and simply leaving the former electrode in place, unused, alongside the replacement.

As an alternative expedient, the prior art embraces adaptor-reducer type connectors functioning as a mechanical interface between the existing pins of a previously implanted electrode catheter and the receiver contacts of a replacement pacemaker; this inevitably reflects a compromise, from technical and medical standpoints alike, as the new implant is impoverished somewhat by the large dimensions of the mechanical components used for the interface. Given the reliance of the patient on the pacemaker, moreover, artificial stimulation must be maintained for the maximum time possible whichever replacement technique is ultimately adopted; accordingly, any replacement operation, and especially the fitment of a mechanical adaptor, must be accomplished as swiftly as possible.

The object of the present invention is to overcome the problem outlined above by providing an adaptor device that can be secured to the unattached end of a unipolar electrode catheter already in situ and used to make the requisite electrical connection to pacemakers of the latest generation; such a device will be simple in embodiment, swiftly implanted in surgery, and able to ensure a suitably dependable connection. Equally, this same object embraces the creation of an electrode catheter with a terminal portion readily adaptable to the markedly compact pacemakers of the latest generation.

SUMMARY of the INVENTION

The stated object is realized in an adaptor device according to the invention, by means of which a previously implanted unipolar electrode catheter can be connected to a replacement cardiac pacemaker of newer and more compact design than the original. By way of preparation, the proximal connecting pin of the existing catheter must be cut and discarded, leaving a loose end of the relative conductor from which the insulating sheath is stripped back to lay bare a length of the spiral wound signal wire. The adaptor comprises: a rigid sleeve accommodating a conductive spindle rotatable about its own axis and rigidly associated with a coaxial stilet that projects from an open socket end of the sleeve and is insertable into the prepared end of the wire; a second spiral wound wire accommodated internally of the sleeve and encompassing the corresponding part of the stilet, which is anchored by its ends to the open socket end and to the spindle, respectively; detachable means by which the spindle is rotated in such a manner as to induce torsion in the second spiral wound wire, thereby occasioning a reduction in diameter of which the effect is to tighten the cut end of the catheter wire against the inserted stilet; an outer sheath of biocompatible material by which the sleeve and the associated components are encapsulated; and fastening means applied over the outer sheath, by which the two connected wires and the stilet are made permanently secure.

BRIEF DESCRIPTION of the DRAWINGS

The invention will now be described in detail, by way of example, with the aid of the accompanying drawings, in which:

FIG. 2 is the side elevation of an adaptor device for electrode catheters according to the invention, viewed partly in section and in a non-operative configuration;

FIG. 3 shows one end of the electrode catheter of FIG. 1, partly in longitudinal section, to which one end of an adaptor device according to the invention is made permanently secure;

DESCRIPTION of the PREFERRED EMBODIMENTS

Figure 1:
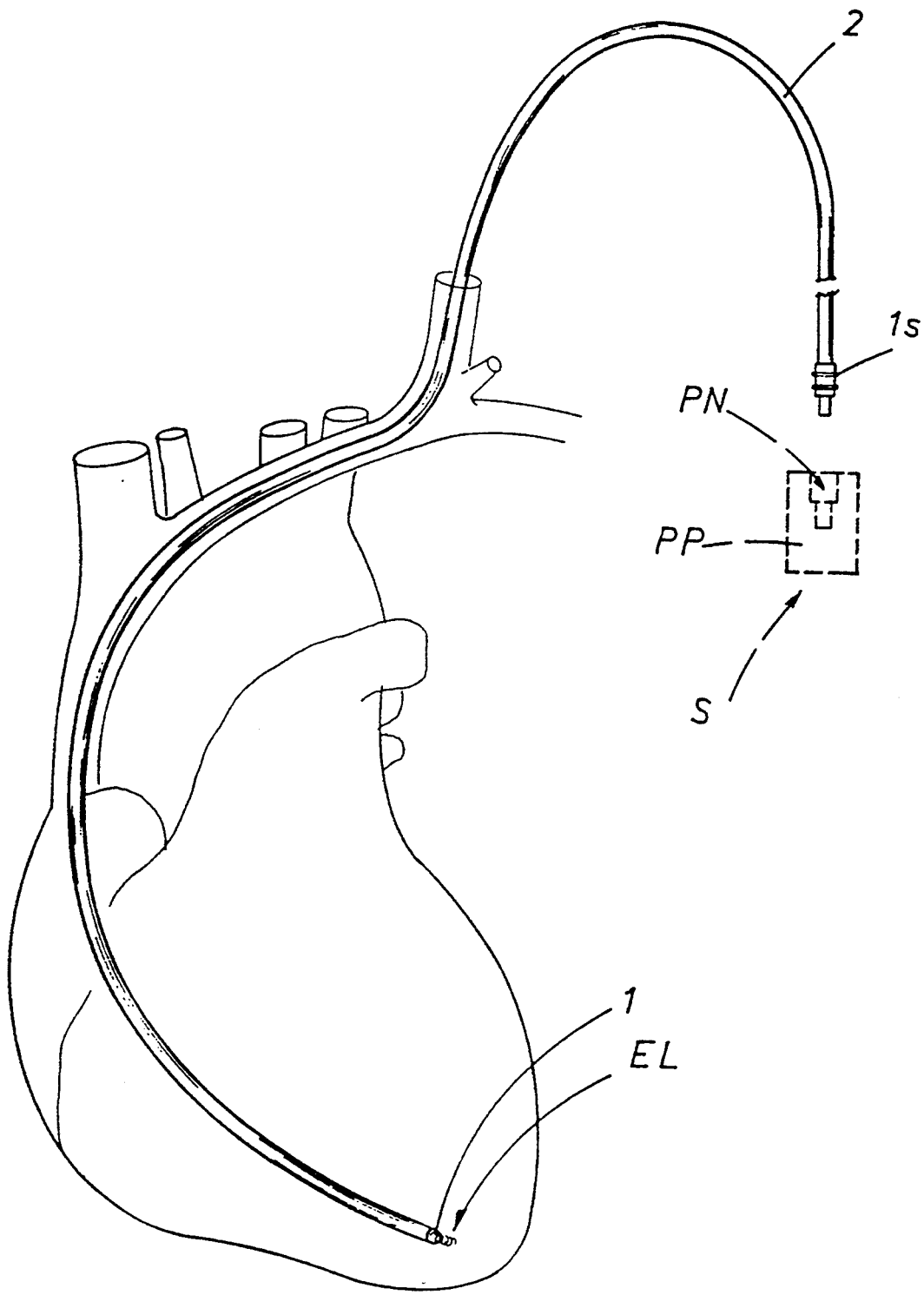
FIG. 1 shows a typical unipolar electrode catheter as conventionally implanted in cardiac muscle.

As illustrated in the drawings, an adaptor device according to the present invention is designed for use in conjunction with cardiac pacemaker electrode catheters of unipolar embodiment, i.e. comprising an internal first conductor of spiral wound wire 1 (see FIG. 1 in particular) connected at one end by a pin 1s to the negative pole PN of a conventional cardiac pacemaker S (illustrated in phantom line) of which the casing provides the positive pole PP of the implant. The first wire 1 is ensheathed by a flexible tube 2 of electrically insulating material and associated at the end remote from the pin 1s with a conductive element EL that constitutes the stimulation electrode, and is offered in direct contact to the cardiac muscle; where appropriate, the element in question can be fashioned in such a manner (for example with a screw tip) as to anchor positively in the wall of the ventricle.

The device according to the invention is viewed in conjunction with an existing electrode catheter of which the original electrode pin 1s aforementioned has been removed, and the sheath 2 cut back a given distance to expose the end ES of the first spiral wound wire 1 (as discernible clearly in FIG. 2). Likewise discernible from FIG. 2, the adaptor device is composed of a sleeve 20, a spindle 3, a stem or stilet 5, a second sheath 4, a second spiral wound wire 6, rotation means 7 and fastening means 8. The spindle 3 is rigid and electrically conductive, and inserted coaxially through the sleeve 20 to an exact fit, rotatable thus about its own axis X; the sleeve in turn is fashioned in a metallic material and exhibits two portions dissimilar in diameter, of which the smaller constitutes a terminal contact element denoted P (in effect, a new pin of diameter smaller than that of the pin is removed from the existing catheter and therefore readily adaptable to the dimensions of the replacement pacemaker), and the larger portion 21 affords an enlarged open end 20a or socket.

At a given point internally of the sleeve 20, the spindle 3 connects or merges directly and coaxially with the stilet 5, which in turn projects a certain distance from the open end 20a of the sleeve 20 and will exhibit an external diameter matched to the internal diameter of the first spiral wound wire 1 in such a way that the one is insertable coaxially into the other.

The second spiral wound wire 6, which likewise is electrically conductive (fashioned preferably from an annealed platinum-iridium alloy, for example), extends through the larger diameter portion 21 of the sleeve and is attached at each end, typically by soldering, to the open end 20a of the sleeve and to the end of the spindle 3 occupying the sleeve 20 (see FIG. 2), respectively; the internal diameter of the second spiral wound wire 6 is substantially identical to the external diameter of the electrode catheter 1, in such a manner that the one can be inserted coaxially into the other.

The rotation means 7 (which are detachable) occupy a position at the end of the spindle 3 that emerges from the smaller diameter portion of the sleeve, and consist in a key 9 rigidly associated with the spindle 3, of which the free end is fashioned as a handle such as can be gripped and turned to rotate the spindle in the sleeve. The key 9 will be seen to afford a slender portion 9s, coinciding with the point of rigid association between key and spindle and serving to define a location at which fracture or separation occurs once a given value of torque is generated by rotation. In practice, the effect of rotating the key, hence the spindle 3 and the second spiral wound wire 6 attached to the spindle, is to generate a torsion by which the diameter of the spiral is reduced, resulting ultimately in a stable retention of the first spiral wound wire 1 between the second wire 6 and the stilet 5, as will become clear in due course.

The components described thus far are accommodated internally of the second sheath 4, which extends at one end beyond the larger diameter portion 21 of the sleeve 20 by a distance approximately equal to the length of the larger diameter portion itself, whilst at the remaining end a given stretch T of the smaller diameter portion of the sleeve 20 will remain exposed, thus providing the terminal contact element P for connection to the pacemaker. The second sheath 4 also affords a pair of sealing rings 11 located adjacent to the exposed stretch T of the sleeve 20 on the catheter side (ensuring a fluid-tight fit between the catheter and the casing of the pacemaker) and two further rings or stops 12 located at the end projecting beyond the sleeve 20; the rings and sheath are fashioned integrally, in a biocompatible material (silicone or similar).

The fastening means 8 consist in external binding elements 10 such as synthetic and/or biocompatible surgical thread applied to a predetermined area of the second sheath 4 compassed by the pair of stop rings 12, in such a way that the electrode cathether is pinched internally of the sheath and retained in a stable position.

The foregoing part of the specification relates to what may be considered as the essential parts of the adaptor, described in their fundamental form. By contrast, the solution illustrated in FIGS. 4, 5, 6 and 7 reflects the typical shape and dimensions of pacemakers currently in use. Here, the end of the sleeve 20 remote from the open socket end 20a affords a lateral branch 25, connected electrically to the main body of the sleeve and projecting at an angle from the relative longitudinal axis, of which the projecting end 25a is exposed from the second sheath 4, providing a pin 1s for connection to the negative pole PN of the pacemaker.

In effect, the branch 25 in question might consist in a third spiral wound wire 27 of which one end is accommodated by a corresponding seat 28 afforded by the sleeve 20, the remaining end being fitted with an electrically conductive pin 29 coinciding, in effect, with the pin 1s destined for connection to the pacemaker S.

Figure 4:
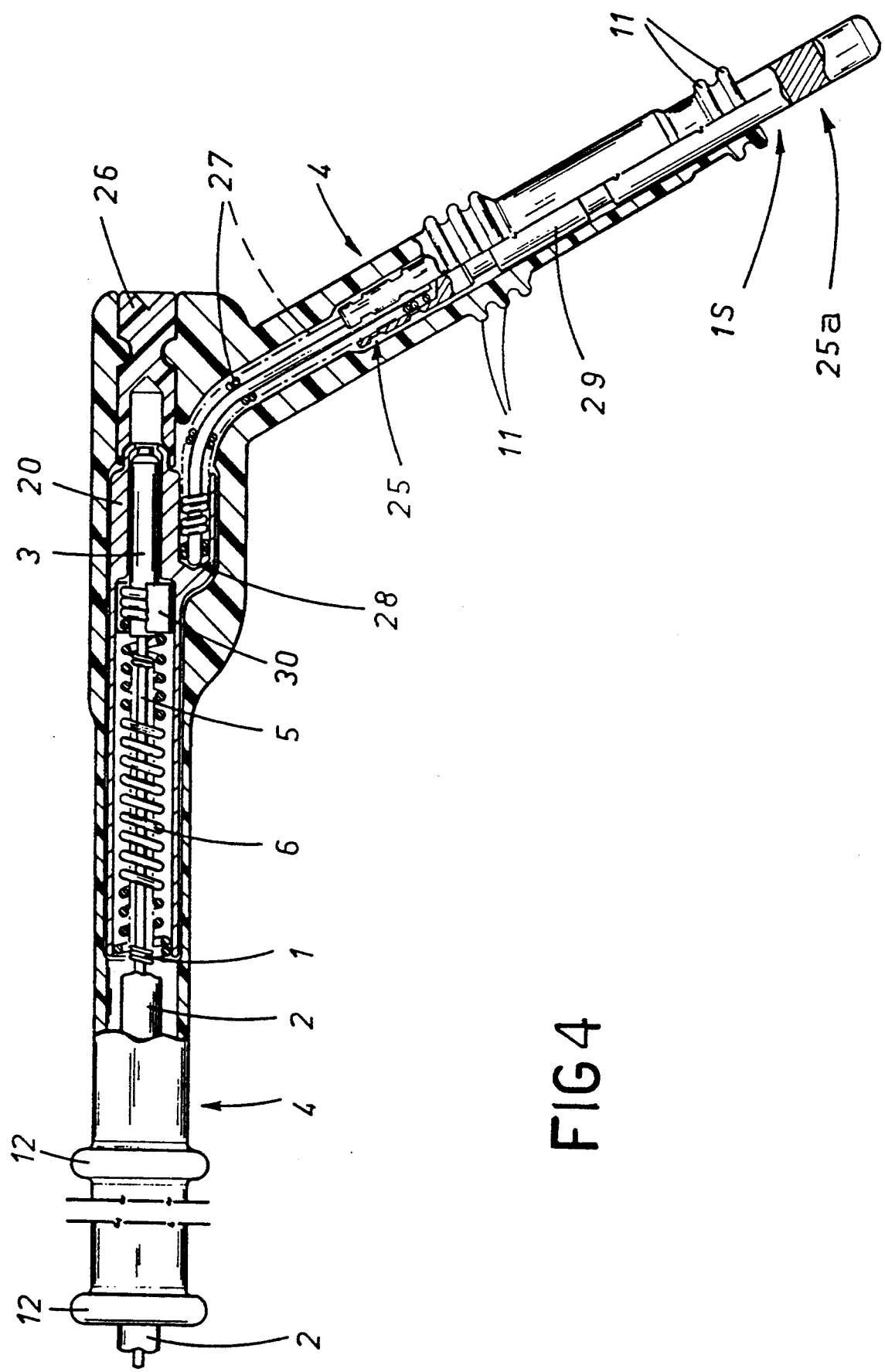
FIG. 4 illustrates an alternative embodiment of the adaptor device shown in the previous drawings, seen in side elevation and partly in section.
Figure 5:
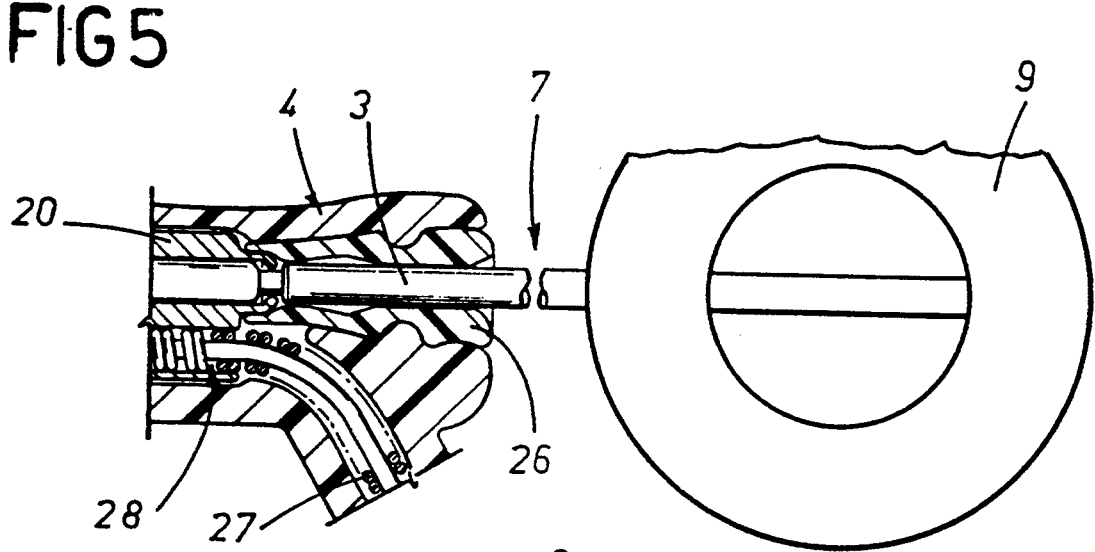
FIG. 5 shows a part of the adaptor device of FIG. 4, seen in side elevation and partly in section, with which detachable means of rotation are associated.
Figure 7:
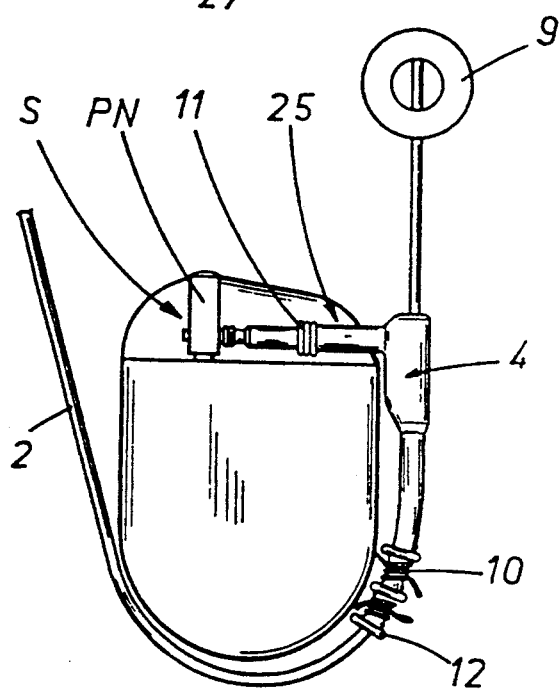
FIGS. 6 and 7 are enlarged side elevations of the alternative embodiment of FIG. 4, illustrating two possible configurations of the connection between the electrode catheter and the cardiac pacemaker.
Figure 6:
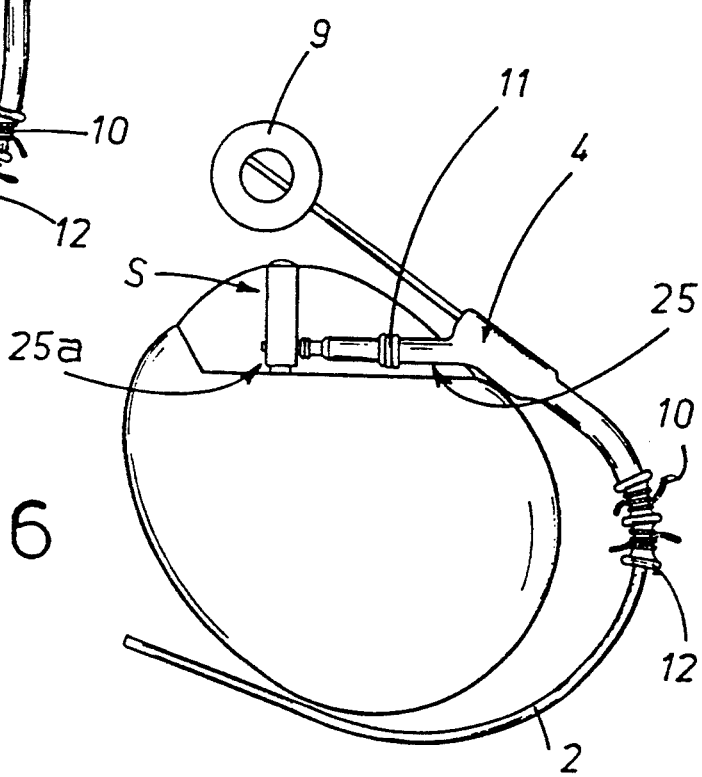

The sleeve 20 in this instance is encapsulated entirely within the second sheath 4, which affords a flexible tubular wall 26 (for example silicone) positioned adjoining the free end of the spindle 3 (associated with the rotation means 7) and coaxial with the sleeve 20, such as will contract and seal the void left at the free end of the spindle 3 by removal of the key (the contracted and expanded configurations of the flexible wall are shown in FIGS. 4 and 5). In this embodiment the second spiral wound wire 6 is secured by means of an electrically conductive collar 30 disposed coaxial with the sleeve 20, which is lodged between the sleeve and the second wire 6 and crimped over the wire against the spindle 3, securing the one to the other. To advantage, this type of solution results in an ergonomically improved configuration of the adaptor device, which is especially effective in ensuring both ease of implantation and swift post-operative adaptability to the patient; in effect, the second sheath 4 might be made to assume different external configurations (see FIGS. 6 and 7), for example, a substantially upturned "L" or right angle profile, or alternatively an obtuse angle, according to the dimensions and geometry of the particular pacemaker implanted.

Parts common to the embodiment of FIGS. 2 and 3 are denoted by the same numbers. The device thus described is fitted and implanted in the following manner.

Having cut off and removed the existing connection pin 1s from the catheter originally implanted in the patient, the first sheath 2 is pared back from the cut end to expose a given length of the first spiral wound wire 1 (preferably a minimum 10 mm), as discernible from FIG. 2.

At this juncture the stilet 5 is inserted coaxially into the first wire 1 to a depth corresponding at least to the length of the portion exposed from the first sheath 2, internally of the projecting end of the second sheath 4 (see arrow F, FIG. 1), such that the first wire 1 is lodged between the stilet 5 and the second wire 6, whereupon the key 9 is rotated (see arrow F1, FIG. 1); the torsional force induced by rotation causes the annealed second wire 6 to shrink in diameter without any elastic tendency to regain its former shape, with the result that the first wire 1 is locked stably against the stilet 5 internally of the second sheath 4 (see FIG. 3). The joining and locking operation thus described is swiftly accomplished, and followed immediately by the step of binding the sheath at the area between the two stop rings 12, thereby pinching the outer second sheath 4 against the inner first sheath 2 and ensuring a fluid-tight seal to protect against any infiltration.

This accomplished, the rotation means 7 are either turned further or subjected to bending stress until a break occurs at the slender portion 9s connecting the key 9 and the spindle 3, whereupon the adaptor is ready for use and can be coupled without delay to the new pacemaker.

With the adaptor thus described and illustrated, an existing unipolar electrode catheter and a cardiac pacemaker of the latest generation can be connected swiftly (the entire sequence of steps described above can be completed in as little as 40 seconds), safely, to the benefit of the patient, and by means of a device which combines simple construction with a capacity for faultless transmission of signals returned from the already implanted electrode.

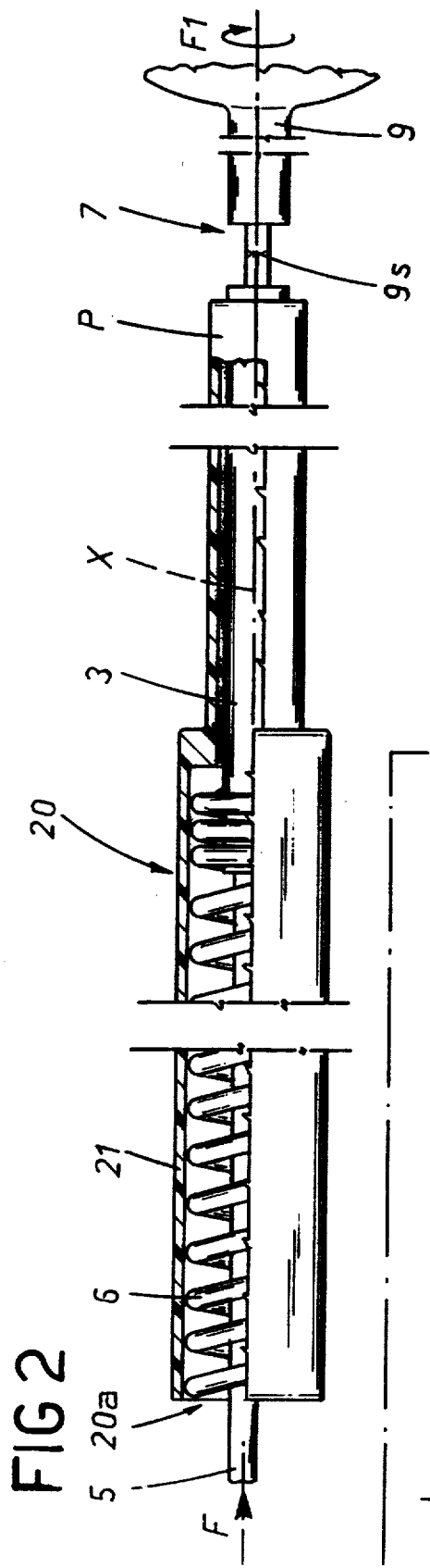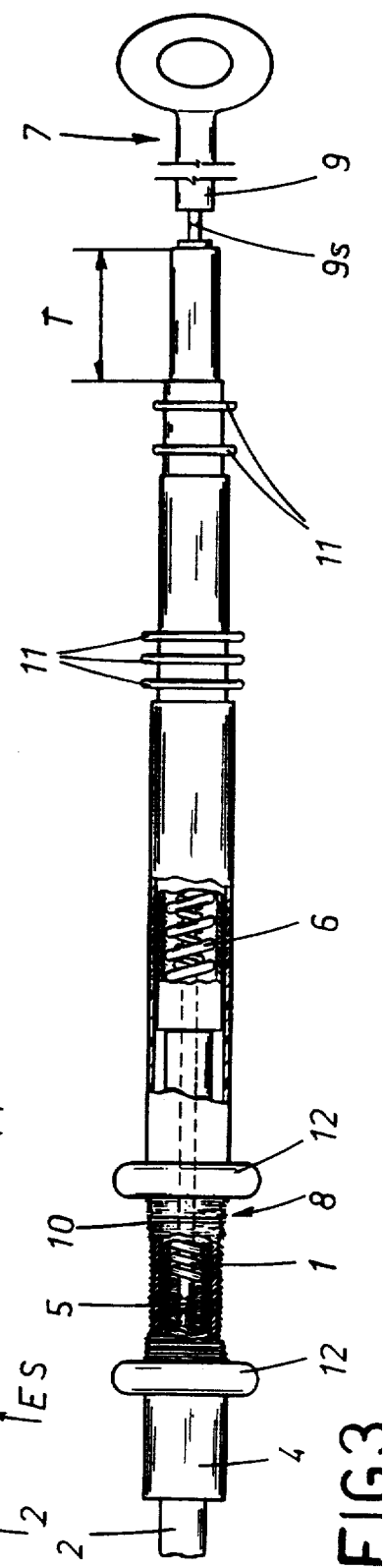

What is claimed:

1. An adaptor device by means of which to connect a cardiac pacemaker to an already implanted unipolar electrode catheter consisting of a first electrically conductive spiral wound wire having a first spiral wound wire end accommodated internally of an insulating flexible tubular sheath, comprising:

an electrically conductive rigid sleeve having an internal surface and with a first sleeve end which coincides with a negative pole if the pacemaker and a second sleeve end which is tubular and affords an open extremity;

an electrically conductive rigid spindle by which the pacemaker is coupled to the electrode catheter, inserted coaxially through and rotatable about its own axis within the sleeve, of which a first spindle end is extended to form a coaxial stilet passing through an beyond the open second sleeve end and insertable coaxially at least into the first spiral wound wire end exposed from the sheath, and a second spindle end remote from the stilet;

a second electrically conductive spiral wound wire having a first end and a second end, interposed between the internal surface of the sleeve, of which the first end is anchored to the internal surface of the sleeve and the second end is anchored to the spindle;

detachable means of rotation, positioned at the second spindle end remote from the stilet and operated . . . and serving to secure the first and the second spiral wound wires permanently together.

2. A device as in claim 1, wherein detachable rotation means consist in a key associated rigidly with the spindle, comprising a removable terminal portion such as can be gripped by hand and turned to rotate the spindle, and a slender portion coinciding with the point of the rigid assocation between key and spindle and designed to fracture once the first and second spiral wound wires are made secure.

3. A device as in claim 1, wherein fastening means consist in binding elements applied externally to an area of the second sheath compassed by a pair of rings in such a manner as to pinch the two spiral wound wires.

4. A device as in claim 1, wherein the sleeve consists substantially in two distinct longitudinal portions exhibiting dissimilar diameters, of which the smaller diameter portion affords a terminal contact element for connection to the negative pole of the pacemaker and the larger diameter portion is embodied in the manner of a socket terminating at the open end second sleeve.

5. A device as in claim 1, wherein the second spiral wound wire is fashioned in an annealed platinum and iridium alloy.

6. A device as in claim 1, wherein the second spiral wound wire is soldered by its first end to the open second sleeve end and by its second end to the second spindle end accommodated internally of the sleeve.

7. A device as in claim 1, comprising the electrically conductive sleeve of which the second sleeve affords a branch, connected electrically to and projecting at an angle from the main body of the sleeve, of which the projecting end is exposed from the second sheath and serves to establish a connection with the negative pole of a pacemaker, wherein the main body of the sleeve is encapsulated entirely within the second tubular sheath affording a flexible tubular wall, disposed coaxial with the sleeve and occupying a position corresponding to that of the detachable rotation means, of which the function is to ensure a hermetic seal of the space occupied by the rotation means following removal of the detachable component of such means.

8. A device as in claim 7, wherein the branch of the sleeve consists in a third spiral wound wire of which an end is accommodated in a corresponding seat afforded by the sleeve, and a third spiral wound wire end associated with an electrically conductive element performing the function of a conventional electrode pin for connection to the pacemaker.

9. A device as in claim 7, wherein the second sheath presents a shape substantially of upturned "L" and right angled profile.

10. A device as in claim 7, wherein the second sheath presents a shape substantially of upturned "L" and obtusely angled profile.

11. A device as in claim 7, comprising the second spiral wound wire positioned internally of the sleeve, of which the first end is secured permanently by means of a collar disposed coaxial with and interposed between the second spiral wound wire and the sleeve.

* * * * *

UNITED STATES PATENT AND TRADEMARK OFFICE
CERTIFICATE OF CORRECTION

PATENT NO. : 5,336,251
DATED : August 9, 1994
INVENTOR(S) : Enzo Borghi

It is certified that error appears in the above-indentified patent and that said Letters Patent is hereby corrected as shown below:

In claim 1 in column 6 at line 5, please delete [...] and replace it with --from externally of the sleeve, of which the function is to induce torsional stress and a consequent reduction in diameter of the second spiral wound wire by rotation of the spindle, in such a way ultimately as to restrain the first spiral wound wire between the second spiral wound wire and the stilet;

- a second tubular sheath of biocompatible and insulating material, by which the sleeve and the second spiral wound wire are concealed at least in part;

- fastening means applied externally to the second sheath over the restrained first spiral wound wire and the restraining second spiral wound wire,--

Signed and Sealed this

Second Day of April, 1996

*Attest:*

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 5,336,251  
DATED : August 9, 1994  
INVENTOR(S) : Enzo Borghi

It is certified that error appears in the above-indentified patent and that said Letters Patent is hereby corrected as shown below:

Sheet 2 of 4 of the drawings, should be deleted to appear as per attached sheet.

In FIGURE 3, numeral 6 is incorrect and should instead be numeral 1 since this is the first wire while numeral 6 should be on the second wire as is shown correctly in FIGURE 2 (enclosed is a corrected FIGURE 3 showing proper numbering for numerals 1 and 6);

At column 5, line 11 and line 13, please change "FIG. 1" to --FIG. 2-- since arrow F and F1 are shown in FIGURE 2, not 1;

At column 5, lines 57-58 in claim 1, please change "an" to --and-- so that it correctly reads the "stilet passing through and beyond", rather than the "stylet passing through an beyond";

At column 6, line 25 in claim 4, please move --end-- to after "open" so that it correctly reads "at the open second sleeve end", rather than "at the open end second sleeve".

Signed and Sealed this

Twenty-ninth Day of October 1996

Attest:

BRUCE LEHMAN

*Attesting Officer*   *Commissioner of Patents and Trademarks*